US011918387B2

(12) United States Patent
Wang et al.

(10) Patent No.: US 11,918,387 B2
(45) Date of Patent: Mar. 5, 2024

(54) INFANT CARE APPARATUS

(71) Applicant: ORIENTAL SYSTEM TECHNOLOGY INC., Hsinchu (TW)

(72) Inventors: Chein-Hsun Wang, Hsin-Chu (TW); Chun-Chiang Chen, Zhubei (TW); Wen-Chie Huang, Hualien County (TW); Ming Le, New Taipei (TW)

(73) Assignee: ORIENTAL SYSTEM TECHNOLOGY INC., Hsinchu (TW)

( * ) Notice: Subject to any disclaimer, the term of this patent is extended or adjusted under 35 U.S.C. 154(b) by 659 days.

(21) Appl. No.: 17/112,651

(22) Filed: Dec. 4, 2020

(65) Prior Publication Data

US 2022/0125391 A1    Apr. 28, 2022

(30) Foreign Application Priority Data

Oct. 27, 2020   (TW) .................................. 109137279

(51) Int. Cl.
| | |
|---|---|
| A61B 5/00 | (2006.01) |
| A61B 5/0205 | (2006.01) |
| A61B 5/11 | (2006.01) |
| G08B 21/02 | (2006.01) |
| A61B 5/024 | (2006.01) |
| A61B 5/08 | (2006.01) |

(52) U.S. Cl.
CPC ............ *A61B 5/746* (2013.01); *A61B 5/0022* (2013.01); *A61B 5/02055* (2013.01); *A61B 5/1113* (2013.01); *A61B 5/7225* (2013.01); *A61B 5/7405* (2013.01); *A61B 5/7455* (2013.01); *G08B 21/0211* (2013.01); *G08B 21/0277* (2013.01); *A61B 5/02444* (2013.01); *A61B 5/0816* (2013.01); *A61B 5/0823* (2013.01); *A61B 5/1102* (2013.01); *A61B 2503/04* (2013.01); *A61B 2560/0214* (2013.01); *A61B 2560/0252* (2013.01); *A61B 2562/0233* (2013.01); *A61B 2562/0271* (2013.01)

(58) Field of Classification Search
CPC ... A61B 5/746; A61B 5/0022; A61B 5/02055; A61B 5/1113; A61B 5/7225; A61B 5/7405; A61B 5/7455; A61B 5/02444; A61B 5/0816; A61B 5/0823; A61B 5/1102; A61B 2503/04; A61B 2560/0252; A61B 2562/0233; A61B 2562/0271; G08B 21/0211; G08B 21/0277
See application file for complete search history.

(56) References Cited

U.S. PATENT DOCUMENTS

| | | | | |
|---|---|---|---|---|
| 2006/0129047 | A1* | 6/2006 | Ruotoistenmaki | G01L 9/008 600/587 |
| 2017/0281017 | A1* | 10/2017 | Halperin | G16H 50/30 |
| 2022/0079514 | A1* | 3/2022 | Main | G06N 3/045 |
| 2022/0087617 | A1* | 3/2022 | Main | G16H 50/20 |

* cited by examiner

*Primary Examiner* — Steven O Douglas
(74) *Attorney, Agent, or Firm* — Muncy, Geissler, Olds & Lowe, P.C.

(57) ABSTRACT

An infant care apparatus includes a piezoelectric sensor and an infrared array sensor. The piezoelectric sensor senses a respiration rate and a heart rate of an infant. The infrared array sensor senses a body temperature and an occupancy state of the infant in a non-contact manner. The abovementioned infant care apparatus can assist in determining an abnormality of the respiration rate and the heart rate of the infant based on the occupancy state of the infant output by the infrared array sensor, so as to reduce a false alarm rate.

16 Claims, 5 Drawing Sheets

INFANT CARE APPARATUS

BACKGROUND OF THE INVENTION

1. Field of the Invention

The present invention relates to a care apparatus, particularly to an infant care apparatus.

2. Description of the Prior Art

Sudden Infant Death Syndrome might be associated with care deficiency or caregiver's imprudence. An infant care apparatus can detect vital signs of an infant, such as respiratory rate, heart rate and body temperature of the infant, and remind the caregiver of taking appropriate measures while the vital sign of the infant is abnormal. Therefore, an infant care apparatus can decrease the risk of sudden infant death.

A conventional infant care apparatus is worn on the ankle of the infant to detect the blood oxygen level and heart rate of the infant, therefore it is inconvenient for the caregiver to undo it frequently. Another conventional infant care apparatus uses an accelerometer to detect the movements of the infant and measure the respiratory rate or the heart rate of infant. However, the conventional infant care apparatus is unlikely to discriminate leaving from ceased breathing which leads to a high false alarm rate that caregiver might neglect it or turn off the alarm. Another conventional infant care apparatus uses microwave to detect the respiratory rate of an infant that cannot detect the heart rate of the infant.

The body temperature of an infant is also a vital sign that should be intensively monitored. A conventional patch-type temperature sensor is attached to forehead of infant to measure the body temperature of an infant. However, the patch-type temperature sensor is a disposable product, which will increase the cost of caring and generate waste. A conventional forehead thermometer cannot accurately measure the body temperature unless it is kept away from the forehead 3-5 cm that cannot accurately detect the body temperature of the infant while turning over during sleep.

Hence, there is a need to provide an infant care apparatus, which can accurately detect the vital signs of infants, including respiratory rates, heart rates and body temperatures, with a low false alarm rate.

SUMMARY OF THE INVENTION

The present invention provides an infant care apparatus, which uses a piezoelectric sensor to detect the respiratory rates and heart rates of infants, and it also uses an infrared array sensor to perform contactless measurement of infant's body temperatures as well as detect the occupancy state of infants to reduce the false alarm rate.

In one embodiment, the present invention proposes an infant care apparatus, which comprises a piezoelectric sensor, an infrared array sensor, a host controller, and an alarm element. The piezoelectric sensor is disposed under a care recipient to detect a respiratory rate and a heart rate of the care recipient and output a corresponding first sensation signal. The infrared array sensor detects the infrared ray radiation of the care recipient to measure the body temperature and occupancy state of the care recipient and output a corresponding second sensation signal. The host controller is electrically connected with the piezoelectric sensor and the infrared array sensor to receive the first sensation signal and the second sensation signal and determine whether at least one of the respiratory rate, heart rate and body temperature of the care recipient is abnormal according to the occupancy state of the care recipient, whereby to output a corresponding control signal. The alarm element is coupled to the host controller and selectively generates an alarm signal recognizable by the user.

The objective, technologies, features and advantages of the present invention will become apparent from the following description in conjunction with the accompanying drawings wherein certain embodiments of the present invention are set forth by way of illustration and example.

BRIEF DESCRIPTION OF THE DRAWINGS

The foregoing conceptions and their accompanying advantages of this invention will become more readily appreciated after being better understood by referring to the following detailed description, in conjunction with the accompanying drawings, wherein.

DESCRIPTION OF THE PREFERRED EMBODIMENTS

Various embodiments of the present invention will be described in detail below and illustrated in conjunction with the accompanying drawings. In addition to these detailed descriptions, the present invention can be widely implemented in other embodiments, and apparent alternations, modifications and equivalent changes of any mentioned embodiments are all included within the scope of the present invention and based on the scope of the Claims. In the descriptions of the specification, in order to make readers have a more complete understanding about the present invention, many specific details are provided; however, the present invention may be implemented without parts of or all the specific details. In addition, the well-known steps or elements are not described in detail, in order to avoid unnecessary limitations to the present invention. Same or similar elements in Figures will be indicated by same or similar reference numbers. It is noted that the Figures are schematic and may not represent the actual size or number of the elements. For clearness of the Figures, some details may not be fully depicted.

Figure 1:
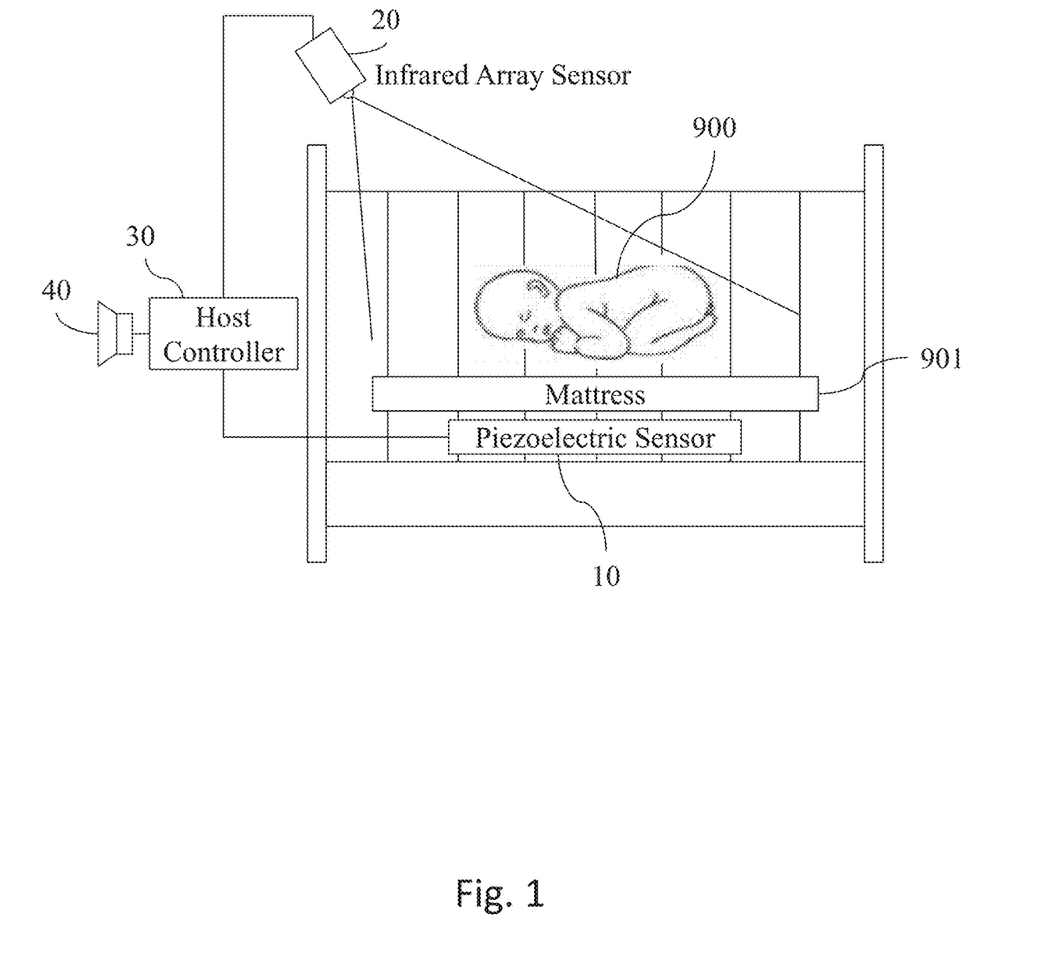
FIG. 1 is a diagram schematically showing an infant care apparatus according to one embodiment of the present invention.

Refer to FIG. 1. In one embodiment, the infant care apparatus of the present invention comprises a piezoelectric sensor 10, an infrared array sensor 20, a host controller 30, and an alarm element 40. The piezoelectric sensor 10 detects a respiratory rate and a heart rate of a care recipient 900 and outputs a corresponding first sensation signal. For example, the care recipient 900 lies on a detection area of the piezoelectric sensor 10, i.e. the piezoelectric sensor 10 is disposed under the care recipient 900; the piezoelectric sensor 10 uses Ballistocardiography technology to detect tiny vibrations caused by respirations and heartbeats of care recipient. For comfort, a mattress 901 may be disposed between the care recipient 900 and the piezoelectric sensor 10. In other words, the care recipient 900 lies on the mattress 901, and the piezoelectric sensor 10 is disposed under the mattress 901 or inside the mattress 901. Considering the detection ranges of the piezoelectric sensor 10 and the infrared array sensor 20, the care recipient 900 is an infant under 3 years old or below 100 cm in height.

The infrared array sensor 20 may receive the infrared ray radiation of the care recipient 900 to measure the body temperature of the care recipient 900 and detect the occupancy state of the care recipient 900 so as to output a corresponding second sensation signal. For example, the infrared array sensor 20 determines whether the care recipient 900 is inside the detection area of the infant care apparatus, i.e. the occupancy state, according to the body temperature detected by the infrared array sensor 20. For example, while the body temperature detected by the infrared array sensor 20 is within a preset range (e.g. between 30 to 40° C.), it is determined that the care recipient 900 is inside the detection area of the infant care apparatus.

The host controller 30 is electrically connected with the piezoelectric sensor 10 and the infrared array sensor 20 and receives the first sensation signal output by the piezoelectric sensor 10 and the second sensation signal output by the infrared array sensor 20. The host controller 30 may determine whether at least one of the respiratory rate, the heart rate and the body temperature is abnormal and output a corresponding control signal. To reduce the false alarm rate, the host controller 30 must use occupancy state from infrared array sensor 20 to generate alarm when the respiration rate and heart rate from the piezoelectric sensor 10 fallen below a predefined threshold value. For example, the piezoelectric sensor 10 does not detect the respiration or heartbeat, the fact may be that the care recipient 900 is taken away from the detection area of the infant care apparatus or that the respiration or heartbeat of the care recipient 900 really interrupts suddenly. In the case that the respiration or heartbeat interrupts, the piezoelectric sensor 10 neither detects any physical value variation nor outputs any signal. However, the infrared array sensor 10 can still detect the body temperature of the care recipient 900. Thus, the host controller 30 can determine that the care recipient 900 is still inside the detection area of the infant care apparatus and further determine that the respiration and heartbeat of the care recipient 900 indeed interruptted. Thereby, the present invention can reduce the false alarm rate significantly.

The alarm element 40 is coupled to the host controller 30 and selectively generates an alarm signal recognizable by the user according to the control signal output by the host controller 30. In one embodiment, the alarm element 40 may be a buzzer or a speaker, able to generate sounds or voices to alarm the caregiver to take appropriate measures. In another embodiment, the alarm element 40 is a light emitting element or a vibratory motor, able to generate lights or vibrations to alarm the caregiver. In further another embodiment, the alarm element 40 is an external electronic device, such as a mobile internet-accessing device or a mobile phone; the host controller 30 uses the control signal to instruct the external electronic device to generate ringing, vibrations, text, voices, or a combination thereof.

Figure 2:
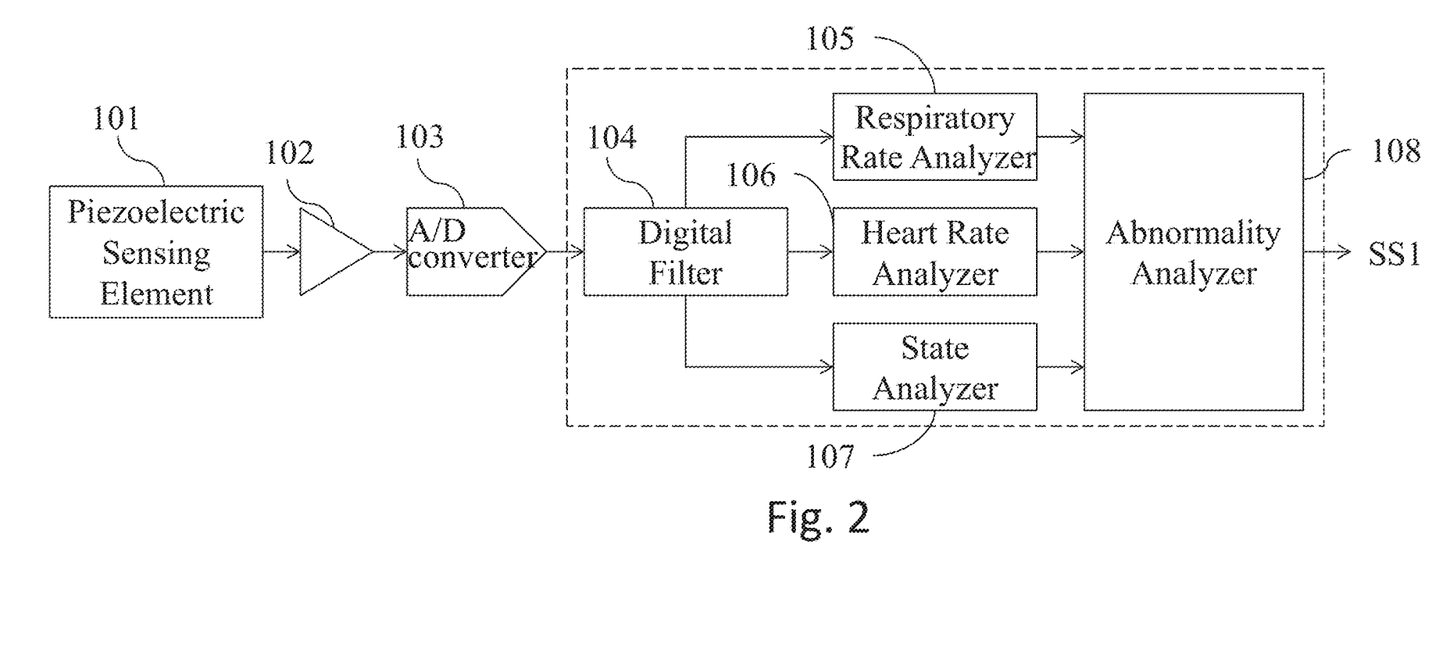
FIG. 2 is a diagram schematically showing a piezoelectric sensor of an infant care apparatus according to one embodiment of the present invention.

Refer to FIG. 2. The piezoelectric sensor 10 of the infant care apparatus of the present invention includes a piezoelectric sensing element 101, a charge amplifier 102, an analog-to-digital converter 103, a digital filter 104, a respiratory rate analyzer 105, a heart rate analyzer 106, and an abnormality analyzer 108. In one embodiment, polyvinylidene fluoride (PVDF) is used to fabricate the piezoelectric sensing element 101 in form of a film; the piezoelectric sensing element 101 is polarized and then disposed on a flexible substrate. According to the Ballistocardiography (BCG), the piezoelectric sensing element 101 detects the physical value variations caused by respirations and heartbeats, converts the physical value variations into charge variations, and then outputs the charge variations in form of an electronic signal. The charge amplifier 102 is electrically connected with the piezoelectric sensing element 101 and converts the electronic signal output by the piezoelectric sensing element 101 into a voltage signal. The analog-to-digital converter 103 is electrically connected with the charge amplifier 102 and converts the voltage signal output by the charge amplifier 102 into a digital signal for the succeeding processing.

The digital filter 104 is electrically connected with the analog-to-digital converter 103 and used to limit the frequency domain range of the digital signal. For example, the frequency domain range of the digital signal is limited to be 0.2-4 Hz to match the fact that the heart rate of an infant is 120-140 times per minute and the respiratory rate of an infant is 35-45 times per minute. The respiratory rate analyzer 105 is electrically connected with the digital filter 104. The respiratory rate analyzer 105 uses a low-pass filter (<1 Hz) to process the digital signal and uses a zero-crossing technology to acquire the respiratory rate of the care recipient 900. The heart rate analyzer 106 is electrically connected with the digital filter 104. The heart rate analyzer 106 uses a high-pass filter (>1 Hz) to process the digital signal and uses a zero-crossing technology to acquire the heartrate rate of the care recipient 900. The abnormality analyzer 108 is electrically connected with the respiratory rate analyzer 105 and the heart rate analyzer 106. The abnormality analyzer 108 determines whether the respiratory rate and heart rate of the care recipient 900 are abnormal and outputs a corresponding first sensation signal SS1 to the host controller 30.

Refer to FIG. 2 again. In one embodiment, the piezoelectric sensor 10 further includes a state analyzer 107, which is electrically connected with the digital filter 104 and the abnormality analyzer 108. The state analyzer 107 determines the motion state, such as the coughs, turn-over, or get-up, of the care recipient 900, according to the digital signal.

It should be explained herein: the analog-to-digital converter 103, the digital filter 104, the respiratory rate analyzer 105, the heart rate analyzer 106, the state analyzer 107 and the abnormality analyzer 108 may be realized with software. Therefore, a microcontroller may execute appropriate programs to realize the abovementioned elements.

Figure 3:
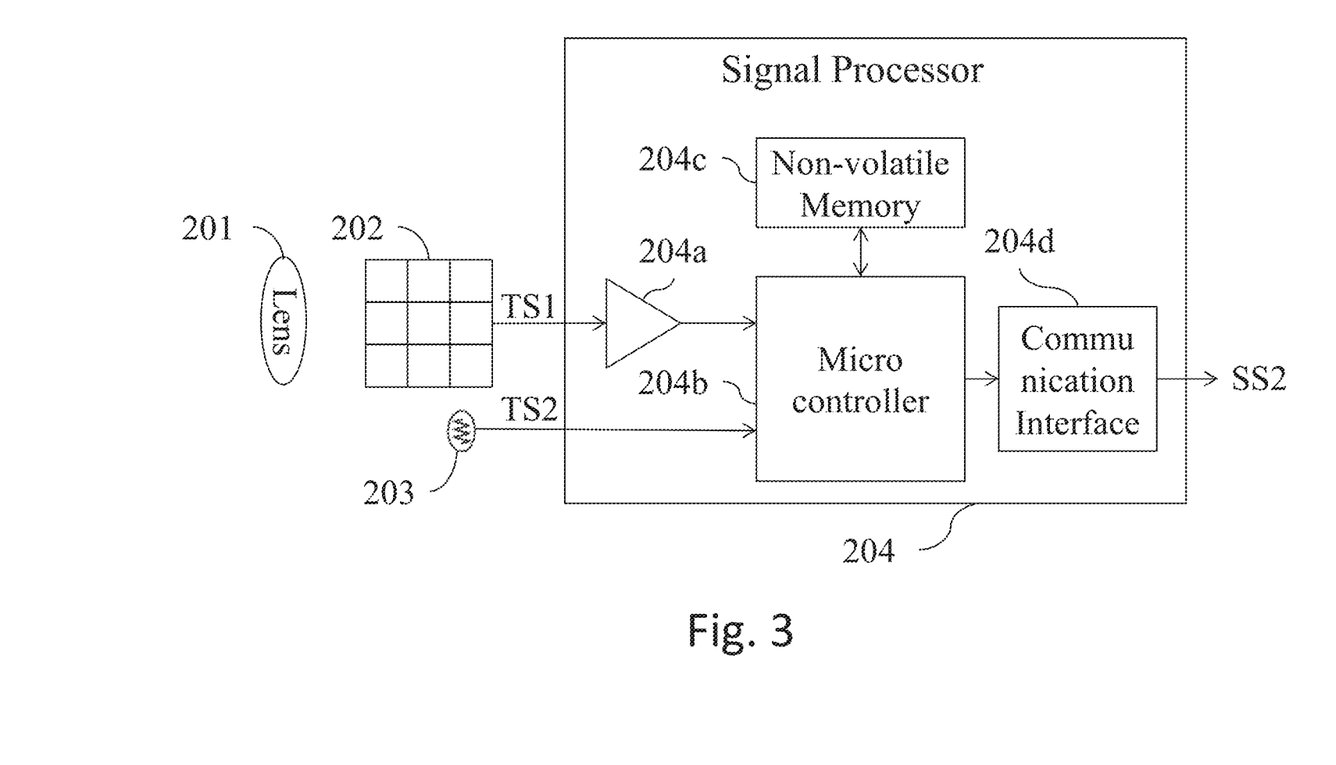
FIG. 3 is a diagram schematically showing an infrared array sensor of an infant care apparatus according to one embodiment of the present invention.

In one embodiment, the infrared array sensor 20 may be a bolometer array sensor or an infrared thermopile array sensor. Refer to FIG. 3. In one embodiment, the infrared array sensor 20 includes a lens 201, a thermopile array chip 202, an ambient temperature sensor 203, and a signal processor 204. The lens 201 defines a sensing angle of the infrared array sensor 20. If a wider area is to be monitored, a wide-angle lens is used as the lens 201, e.g. the lens 201 has a sensing angle of 38-90 degrees. In one embodiment, the lens 201 has a sensing angle of 60 degrees. In design of a lens, a wide-view angle lens is more likely to be realized. In one embodiment, the lens 201 is made of silicon, germanium, sapphire, or zinc selenide, allowing a light beam with a wavelength range of 1-14 µm to pass through. In one embodiment, the lens 201 is a silicon-based Fresnel lens or a reflective lens where a plastic substrate is coated with a metallic layer.

The thermopile array chip 202 is disposed at one side of the lens 201, receiving the infrared ray within the range of the sensing angle and outputting an infrared sensation signal TS1. In one embodiment, the thermopile array chip 202 has a resolution of 8×8, 16×16, 32×32, 64×64, or 128×128 pixels. In response to the instruction of the signal processor 204, the thermopile array chip 202 may send back the infrared sensation signals of corresponding pixels. The ambient temperature sensor 203 detects the ambient temperature and outputs a corresponding ambient temperature sensation signal TS2. In cooperation with the ambient temperature sensor 203, the thermopile array chip 202 may obtain more accurate temperature sensation results of infant's body temperature. In one embodiment, the ambient temperature sensor 203 is a silicon-based temperature sensor integrated with the thermopile array chip 202. In another embodiment, the ambient temperature sensor 203 is a thermistor independent from the thermopile array chip 202. The signal processor 204 is electrically connected with the thermopile array chip 202 and the ambient temperature sensor 203. The signal processor 204 processes the infrared sensation signal TS1 output from the thermopile array chip 202 as well as the ambient temperature sensation signal TS2 output from the ambient temperature sensor 203 and outputs a calculated second sensation signal SS2.

In one embodiment, the signal processor 204 includes a signal amplifier 204a, a microcontroller 204b, a non-volatile memory 204c and a communication interface 204d. The thermopile array chip 202 outputs the infrared sensation signal TS1 to the signal amplifier 204a. The infrared sensation signal TS1 is amplified and transmitted to the microcontroller 204b. An analog-to-digital converter, which is built in the microcontroller 204b, converts the infrared sensation signal TS1, which is output by the thermopile array chip 202, into a digital signal. Similarly, the analog-to-digital converter converts the ambient temperature sensation signal TS2, which is output from the ambient temperature sensor 203, to obtain the ambient temperature. The non-volatile memory 204c is used to store calibration parameters of the thermopile array chip 202 and parameters of the ambient temperature sensor 203, which are used to work out the value of the measured body temperature. The non-volatile memory 204c is also used to store the programs for verifying the abnormality of the body temperature and ceasing of breath or heart rate of infant. The communication interface 204d outputs the second sensation signal SS2 to the host controller 30. The communication interface 204d may be an Inter-Integrated Circuit Bus (VC), a Universal Asynchronous Receiver/Transmitter (UART), a Serial Peripheral Interface (SPI), a Universal Serial Bus (USB), an analog voltage-type I/O port or a logic I/O port. It is easily understood: the non-volatile memory 204c and the communication interface 204d may be built in the microcontroller 204b, such as the STM8L151G6U6 microcontroller.

It should be explained herein: the body temperature detected by the infrared array sensor 20 is the skin temperature of the care recipient 900, which is different from the core temperature of the care recipient 900. Therefore, whether the body temperature of the care recipient 900 is abnormal is determined according to the ratio or relative values of the skin temperatures. For example, while the difference between a reference value and the body temperature of the care recipient 900, which was measured latest, is greater than or equal to 1.5° C., it is determined that the body temperature of the care recipient 900 is abnormal. In one embodiment, the reference value is the value of the body temperature of the care recipient 900, which was measured latest. In another embodiment, the reference value is the moving average of a plurality of body temperatures of the care recipient 900, which are measured within an interval of time. For example, the peak value measured by the infrared array sensor 20 is used as a single measured value; the measurement is performed each minute; the 30 pieces of measured values obtained in the past 30 minutes are averaged to obtain the average value of the body temperatures measured in the past 30 minutes, and the average value is used as the reference value. In order to decrease the influence of noise, each recorded body temperature may be obtained via averaging a plurality of measured values. For example, the infrared array sensor 20 undertakes sampling once per second, and 60 pieces of samples are averaged to obtain the average body temperature as the final measured body temperature of the past one minute. In one embodiment, while the body temperature measured latest is smaller than or equal to a second preset value (such as 30° C.), it may be determined that the care recipient 900 has left the detection area of the infrared array sensor 20. In such a case, a corresponding occupancy state, such a logic value "0", is output. In one embodiment, an occupancy state may be realized with a switch (such as a metal-oxide-semiconductor field-effect transistor (MOSFET)).

Figure 4:
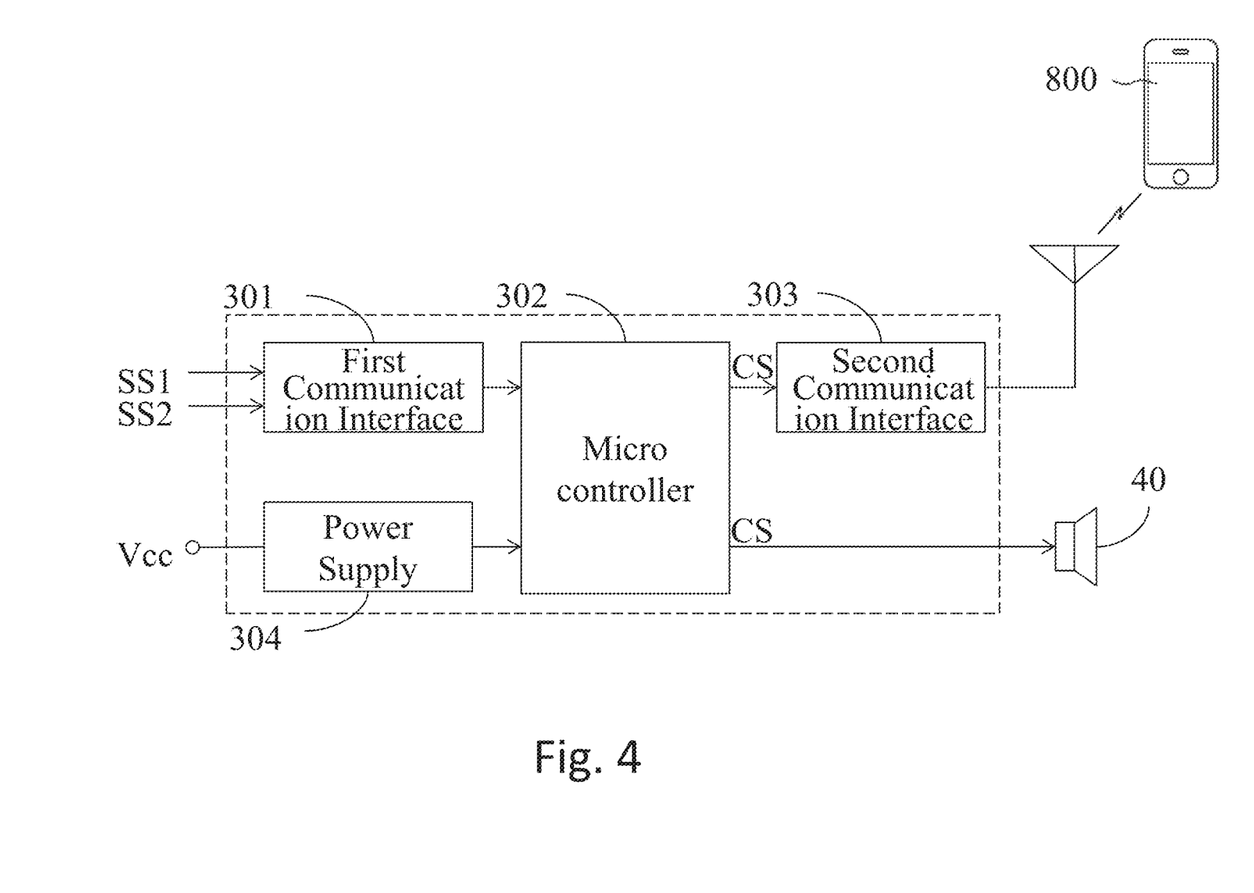
FIG. 4 is a diagram schematically showing a host controller of an infant care apparatus according to one embodiment of the present invention.

Refer to FIG. 4. In one embodiment, the host controller 30 of the infant care apparatus of the present invention includes a first communication interface 301, a microcontroller 302, a second communication interface 303 and a power supply 304. The power supply 304 provides power Vcc required by the operation of the infant care apparatus, including the power required by the operation of the host controller 30, the piezoelectric sensor 10 and the infrared array sensor 20. The first communication interface 301 is electrically connected with the piezoelectric sensor 10 and the infrared array sensor 20 to receive the first sensation signal SS1 output by the piezoelectric sensor 10 and the second sensation signal SS2 output by the infrared array sensor 20. In one embodiment, the first communication interface 301 may be an Inter-Integrated Circuit Bus (VC), a Universal Asynchronous Receiver/Transmitter (UART), a Serial Peripheral Interface (SPI), a Universal Serial Bus (USB), an analog voltage-type I/O port or a logic I/O port. The microcontroller 302 is electrically connected with the first communication interface 301, processing the first sensation signal SS1 and the second sensation signal SS2 and outputting a corresponding control signal CS to control the action of the alarm element 40. The second communication interface 303 is electrically connected with the microcontroller 302, whereby the infant care apparatus can undertake wireless communication with an external electronic device 800 through the second communication interface 303. For example, the external electronic device 800 may be a mobile internet-accessing device or a mobile phone; while the respiratory rate, heart rate or body temperature of the care recipient 900 is abnormal, the host controller 30 may use the control signal CS to demand the external electronic deice 800 to output rings, vibrations, text, voices or a combination thereof to remind the caregiver to take appropriate measures. In one embodiment, the second communication interface 303 may be realized with a wireless area network communication protocol, a Bluetooth communication protocol, or a Sub-1 GHz radio frequency communication protocol.

As mentioned above, a microcontroller may execute appropriate programs to realize the analog-to-digital converter 103, the digital filter 104, the respiratory rate analyzer 105, the heart rate analyzer 106, the state analyzer 107, and the abnormality analyzer 108 of the piezoelectric sensor 10.

Figure 5:
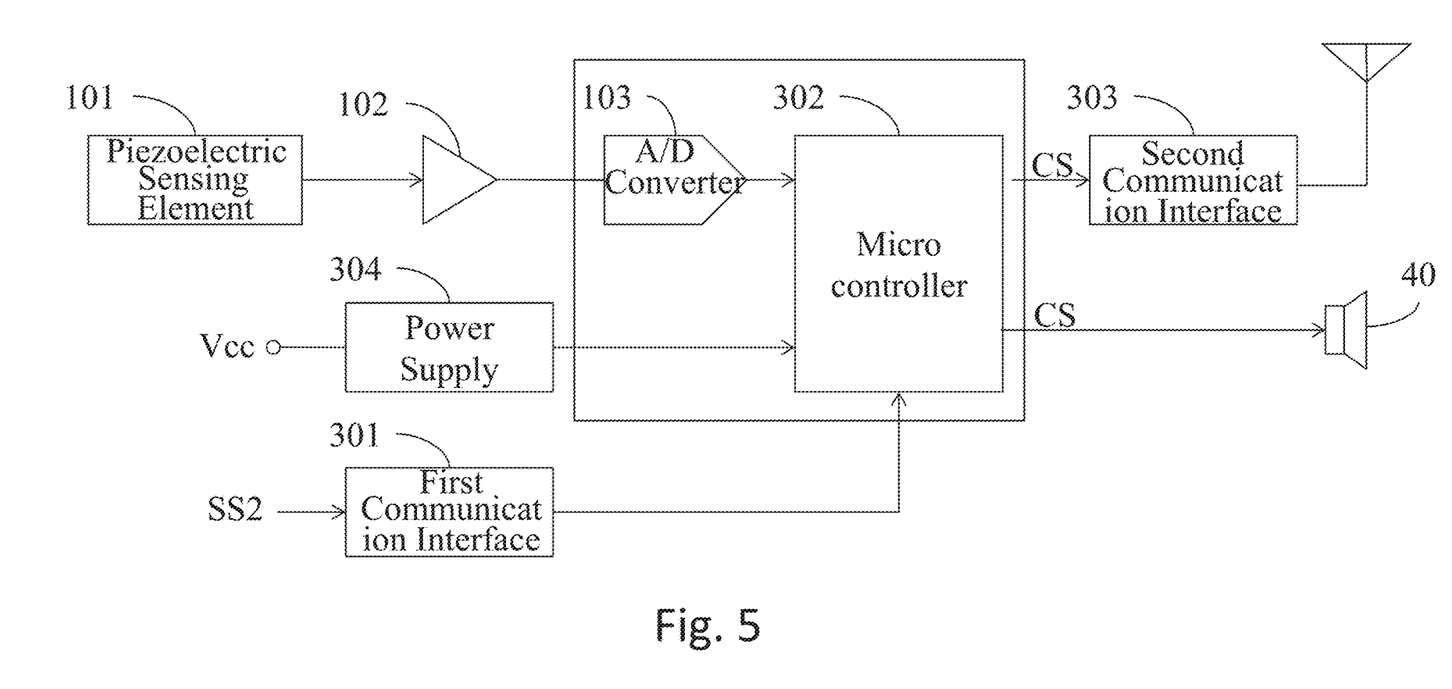
FIG. 5 is a diagram schematically showing an infant care apparatus according to another embodiment of the present invention.

Therefore, the piezoelectric sensor 10 and the host controller 30 may be integrated together and may share a common microcontroller. Refer to FIG. 5. In one embodiment, the analog-to-digital converter 103 and the microcontroller 302 are integrated into a single chip. According to the architecture shown in FIG. 5, the piezoelectric sensing element 101, the charge amplifier 102, the analog-to-digital converter 103 and the microcontroller 302 may be used to realize the function of the piezoelectric sensor 10, i.e. detecting the respiratory rate and heart rate of the care recipient 900. Further, the first communication interface 301, the microcontroller 302, the second communication interface 303 and the power supply 304 may be used to realize the function of the host controller 30, wherein the host controller 30 receives the first sensation signal SS1 output by the infrared array sensor 20 through the first communication interface 301; the host controller 30 uses the control signal CS to trigger the alarm element 40 or transmits the control signal through the second communication interface 303 to the external electronic device 800.

In conclusion, the present invention proposes an infant care apparatus, which uses a piezoelectric sensor to detect the respiratory rate and heart rate of an infant and uses an infrared array sensor to detect the body temperature and occupancy state of the infant in a contactless way, wherein the occupancy state may assist in determining whether the respiratory rate and heart rate of the infant is abnormal, whereby the false alarm rate of warning an abnormal respiratory rate or heat rate is reduced.

While the invention is susceptible to various modifications and alternative forms, a specific example thereof has been shown in the drawings and is herein described in detail. It should be understood, however, that the invention is not to be limited to the particular form disclosed, but to the contrary, the invention is to cover all modifications, equivalents, and alternatives falling within the appended claims.

What is claimed is:

1. An infant care apparatus, comprising:
    a piezoelectric sensor, disposed under a care recipient, detecting a respiratory rate and a heart rate of the care recipient, and outputting a corresponding first sensation signal;
    an infrared array sensor, receiving an infrared ray radiation from the care recipient to measure a body temperature and an occupancy state of the care recipient, and outputting a corresponding second sensation signal;
    a host controller, electrically connected with the piezoelectric sensor and the infrared array sensor, receiving the first sensation signal and the second sensation signal, and determining whether at least one of the respiratory rate, the heart rate and the body temperature of the care recipient is abnormal according to the occupancy state of the care recipient and the outputting a corresponding control signal; and
    an alarm element, coupled to the host controller, and selectively generating an alarm signal recognizable by a user according to the control signal.

2. The infant care apparatus according to claim 1, wherein the piezoelectric sensor includes a piezoelectric element, made from polyvinylidene fluoride (PVDF).

3. The infant care apparatus according to claim 1, wherein the piezoelectric sensor includes:
    a piezoelectric element, made of polyvinylidene fluoride (PVDF), used to detect physical value variations caused by respirations or heartbeats of the care recipient, and outputting a corresponding electronic signal;
    a charge amplifier, electrically connected with the piezoelectric element, and converting the electronic signal output by the piezoelectric element into a voltage signal;
    an analog-to-digital converter, electrically connected with the charge amplifier, and converting the voltage signal output by the charge amplifier into a digital signal;
    a digital filter, electrically connected with the analog-to-digital converter, and limiting a frequency domain range of the digital signal;
    a respiratory rate analyzer, electrically connected with the digital filter, and analyzing the respiratory rate of the care recipient according to the digital signal;
    a heart rate analyzer, electrically connected with the digital filter, and analyzing the heart rate of the care recipient according to the digital signal; and
    an abnormality analyzer, electrically connected with the respiratory rate analyzer and the heart rate analyzer, determining whether the respiratory rate and the heart rate of the care recipient is abnormal, and outputting the corresponding first sensation signal.

4. The infant care apparatus according to claim 3, wherein the analog-to-digital converter, the digital filter, the respiratory rate analyzer, the heart rate analyzer and the abnormality analyzer are realized by a microcontroller.

5. The infant care apparatus according to claim 3, wherein the piezoelectric sensor further includes:
    a state analyzer, electrically connected with the digital filer and the abnormality analyzer, and determining a motion state of the care recipient according to the digital signal.

6. The infant care apparatus according to claim 1, wherein the host controller includes:
    a first communication interface, electrically connected with the piezoelectric sensor and the infrared array sensor to receive the first sensation signal and the second sensation signal;
    a microcontroller, electrically connected with the first communication interface, processing the first sensation signal and the second sensation signal, and outputting the corresponding control signal;
    a second communication interface, electrically connected with the microcontroller to enable the infant care apparatus to undertake a wireless communication with an external electronic device through the second communication interface; and
    a power supply, providing power for the infant care apparatus.

7. The infant care apparatus according to claim 6, wherein the piezoelectric sensor and the host controller share the microcontroller.

8. The infant care apparatus according to claim 6, wherein the first communication interface includes an Inter-Integrated Circuit Bus (I2C), a Universal Asynchronous Receiver/Transmitter (UART), a Serial Peripheral Interface (SPI), a Universal Serial Bus (USB), an analog voltage-type I/O port or a logic I/O port.

9. The infant care apparatus according to claim 6, wherein the second communication interface is realized with a wireless area network communication protocol, a Bluetooth communication protocol, or a Sub-1 GHz radio frequency communication protocol.

10. The infant care apparatus according to claim 1, wherein the infrared array sensor includes an infrared thermopile array sensor.

11. The infant care apparatus according to claim 1, wherein the infrared array sensor has a resolution of 8×8, 16×16, 32×32, 64×64, or 128×128 pixels.

12. The infant care apparatus according to claim 1, wherein the infrared array sensor includes:
- a lens, defining a sensing angle of the infrared array sensor;
- a thermopile array chip, disposed on one side of the lens, receiving the infrared ray within the sensing angle of the infrared array sensor, and outputting an infrared sensation signal;
- an ambient temperature sensor, detecting an ambient temperature, and outputting an ambient temperature sensation signal; and
- a signal processor, electrically connected with the thermopile array chip and the ambient temperature sensor, and outputting the corresponding second sensation signal according to the infrared sensation signal and the ambient temperature sensation signal.

13. The infant care apparatus according to claim 12, wherein the ambient temperature sensor is a thermistor independent from the thermopile array chip or a silicon-based temperature sensor integrated with the thermopile array chip.

14. The infant care apparatus according to claim 12, wherein the lens is made of silicon, germanium, sapphire, or zinc selenide.

15. The infant care apparatus according to claim 12, wherein the lens is a silicon-based Fresnel lens or a reflective lens where a plastic substrate is coated with a metal layer.

16. The infant care apparatus according to claim 1, wherein the alarm signal is light, sound, vibrations, text, voices, or a combination thereof.

* * * * *